(12) United States Patent
Van Eperen

(10) Patent No.: US 7,204,899 B2
(45) Date of Patent: Apr. 17, 2007

(54) APPARATUS AND METHOD FOR MECHANICALLY BONDING AND CUTTING AN ARTICLE

(75) Inventor: David J. Van Eperen, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 352 days.

(21) Appl. No.: 10/426,614

(22) Filed: Apr. 30, 2003

(65) Prior Publication Data

US 2004/0216830 A1 Nov. 4, 2004

(51) Int. Cl.
*B32B 37/00* (2006.01)
(52) U.S. Cl. .................. 156/73.3; 156/73.1; 156/269; 156/290; 156/308.4
(58) Field of Classification Search ........... 156/73.1, 156/73.3, 251, 253, 267, 269, 290, 308.2, 156/308.4, 555, 580.1, 580.2, 582, 583.1, 156/522; 264/442, 443, 444, 445; 425/174.2
See application file for complete search history.

(56) References Cited

U.S. PATENT DOCUMENTS

| | | | |
|---|---|---|---|
| 3,438,835 A * | 4/1969 | Chen et al. ............. | 156/522 |
| 3,874,975 A | 4/1975 | Lagain | |
| 3,939,033 A | 2/1976 | Grgach et al. | |
| 4,158,584 A | 6/1979 | Clarke et al. | |
| 4,436,576 A * | 3/1984 | Seiden ................ | 156/543 |
| 4,663,220 A | 5/1987 | Wisneski et al. | |
| 4,690,722 A | 9/1987 | Flood | |
| 4,704,116 A | 11/1987 | Enloe | |
| 4,940,464 A | 7/1990 | Van Gompel et al. | |
| 5,046,272 A | 9/1991 | Vogt et al. | |
| 5,096,532 A | 3/1992 | Neuwirth et al. | |
| 5,104,116 A | 4/1992 | Pohjola | |
| 5,110,403 A | 5/1992 | Ehlert | |
| 5,224,405 A | 7/1993 | Pohjola | |
| 5,226,992 A | 7/1993 | Morman | |
| 5,552,013 A * | 9/1996 | Ehlert et al. ........... | 156/555 |
| 5,660,666 A | 8/1997 | Dilnik et al. | |
| 5,707,470 A | 1/1998 | Rajala et al. | |
| 5,766,389 A | 6/1998 | Brandon et al. | |
| 5,858,515 A | 1/1999 | Stokes et al. | |

(Continued)

FOREIGN PATENT DOCUMENTS

DE 1560128 2/1971

(Continued)

OTHER PUBLICATIONS

International Search Report PCT/US2004/001411, dated Jun. 8, 2004, 3 pages.

*Primary Examiner*—James Sells
(74) *Attorney, Agent, or Firm*—Senniger Powers

(57) ABSTRACT

In a method and apparatus for mechanically bonding and cutting an article during assembly thereof at least a portion of the article is transported through a nip defined by first and second members. A bonding segment is disposed on one of the first and second members and a cutting segment separate from the bonding segment is also disposed on one of the first and second members. The apparatus is operable so that a portion of the article is mechanically bonded as the article passes through the nip and a portion of the article separate from the bonded portion is cut as the article passes through the nip.

16 Claims, 10 Drawing Sheets

U.S. PATENT DOCUMENTS

| | | |
|---|---|---|
| 5,906,694 A | 5/1999 | Duly |
| 5,985,065 A | 11/1999 | Kling |
| 6,098,684 A | 8/2000 | Terawaki |
| 6,149,755 A | 11/2000 | McNichols et al. |
| 6,165,298 A | 12/2000 | Samida et al. |
| 6,277,224 B1 * | 8/2001 | Muesch et al. ............ 156/73.3 |
| 6,451,205 B1 | 9/2002 | McGaw, Jr. |
| 6,562,167 B2 | 5/2003 | Coenen et al. |
| 2002/0000291 A1 | 1/2002 | Coenen et al. |
| 2002/0197345 A1 * | 12/2002 | Kubik et al. ............ 425/174.2 |

FOREIGN PATENT DOCUMENTS

| | | |
|---|---|---|
| DE | 3609999 | 10/1986 |
| EP | 0 217 032 B1 | 2/1992 |
| WO | WO 00/37009 A2 | 6/2000 |
| WO | WO 00/37009 A3 | 6/2000 |
| WO | WO 01/87211 A2 | 11/2001 |
| WO | WO 01/88245 A2 | 11/2001 |

* cited by examiner

APPARATUS AND METHOD FOR MECHANICALLY BONDING AND CUTTING AN ARTICLE

BACKGROUND OF THE INVENTION

This invention relates generally to articles such as training pants, diapers, feminine hygiene products, incontinence garments, material webs and the like, and more particularly to apparatus and methods for mechanically bonding and cutting such articles during assembly thereof.

Articles such as absorbent articles find widespread use as personal care products including, without limitation, diapers, children's toilet training pants, adult incontinence garments, sanitary napkins and the like, as well as surgical bandages and sponges. These articles absorb and contain body waste and are usually intended to be discarded after a limited period of use, i.e., the articles are not intended to be laundered or otherwise restored for reuse. Conventional absorbent articles comprise an absorbent body disposed between a liner, which contacts the wearer's skin, and an outer cover, which inhibits liquid body waste absorbed by the absorbent body from leaking out of the article. The liner of the absorbent article is typically liquid permeable to permit liquid body waste to pass therethrough for absorption by the absorbent body.

Conventional absorbent articles also typically include some type of fastening system for securing the absorbent article in an assembled configuration and/or for fitting the article on the wearer, such as on the wearer's waist in the case of diapers and training pants. In many such applications, the fastening system is releasable and refastenable so that the article can be temporarily removed and then refastened to the wearer.

One common form of fastening system is the so-called hook-and-loop fastening system, which comes in various forms and has both advantages and disadvantages in its application to such absorbent articles. For example, particularly when used for training pants, engageable hook and loop fasteners are secured respectively to the front and back waist regions of the article generally at overlapping side panels of the article so that the fasteners releasably engage each other to form the three dimensional shape of the article. In typical such articles, the loop fastener may form a portion of the article itself or be attached to the side panel or other component of the article. The hook fastener is generally attached to an extensible substrate (e.g., the side panel) so that it can be suitably positioned in engagement with the loop fastener material while allowing for various shapes and sizes of the intended wearers of the article.

Conventional apparatus for making absorbent articles such as children's training pants or diapers assemble the various components, such as the liner, outer cover, absorbent body, side panels (e.g., in training pants) and fastening system (e.g. a hook and loop fastening system). It is known to ultrasonically bond the fastening system to a substrate such as the liner, outer cover and/or side panels. For example a rotary ultrasonic bonding device comprising a rotary anvil roll and corresponding horn roll may be used. The anvil roll has a plurality of pins protruding therefrom about its circumference to thermally bond the fastening system to the substrate at discrete bond points.

The partially assembled article is often subsequently trimmed during manufacture, e.g., by cutting out a portion of the outer edge of the liner, outer cover and/or side panels, to provide desired form-fitting features of the article, such as the leg openings of diapers and training pants. A die cutting assembly, separate from the anvil roll and horn, is typically positioned downstream of the anvil roll for cutting the article, such as to form a tapered leg end edge of the side panels.

SUMMARY OF THE INVENTION

In one embodiment a method of the present invention for mechanically bonding and cutting an article during assembly thereof generally comprises transporting the article in a machine direction during assembly thereof such that at least part of the article passes through a nip as the article is transported in the machine direction. A portion of the article is mechanically bonded as the article passes through the nip. A portion of the article separate from the bonded portion is cut as the article passes through the nip.

Apparatus of one embodiment of the present invention for mechanically bonding and cutting an article upon movement of the article in a machine direction generally comprises a first member and a second member arranged relative to the first member to define a nip therebetween for receiving the article therethrough upon movement of the article in the machine direction. A bonding segment is disposed on one of the first and second members and is configured for mechanically bonding the article. A cutting segment is also disposed on one of the first and second members and is configured for cutting the article. The apparatus is operable in a bonding mode in which the nip is defined in part by the bonding segment and the cutting segment is disposed external of the nip such that a portion of the article is mechanically bonded as the article passes through the nip. The apparatus is also operable in a cutting mode in which the nip is defined in part by the cutting segment and the bonding segment is disposed external of the nip whereby a portion of the article other than the bonded portion thereof is cut as the article passes through the nip.

In another embodiment, the apparatus generally comprises a first member and a second member arranged relative to the first member to define a nip therebetween for receiving the article therethrough upon movement of the article in the machine direction. A bonding segment is disposed on one of the first and second members and is configured for mechanically bonding the article. A cutting segment is disposed on one of the first and second members separate from the bonding segment and is configured for cutting the article. The apparatus is operable to position the first and second members relative to each other at the nip such that at least one of the bonding segment and the cutting segment at least partially defines the nip as the article passes therethrough.

DEFINITIONS

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Extensible" refers to a material or composite that is stretchable or capable of being elongated in at least one direction, but which may not have sufficient recovery to be considered elastic.

"Flexible" refers to materials which are compliant and which will readily conform to the general shape and contours of the wearer's body.

"Force" includes a physical influence exerted by one body on another which produces acceleration of bodies that are free to move and deformation of bodies that are not free to move. Force is expressed in grams per unit area.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 degrees are designated "wettable" or hydrophilic, while fibers having contact angles greater than 90 degrees are designated "nonwettable" or hydrophobic.

"Integral" is used to refer to various portions of a single unitary element rather than separate structures bonded to or placed with or placed near one another.

"Inward" and "outward" refer to positions relative to the center of an article, and particularly transversely and/or longitudinally closer to or away from the longitudinal and transverse center of the article.

"Layer" when used in the singular can have the dual meaning of a single element or a plurality of elements.

"Longitudinal" and "transverse" have their customary meaning, as indicated by the longitudinal and transverse axes depicted in FIGS. 2 and 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Nonwoven" and "nonwoven web" refer to materials and webs of material which are formed without the aid of a textile weaving or knitting process.

"Operatively joined," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either direct, such as by joining the member directly to an element, or can be indirect, such as by means of another member disposed between the member and the element.

"Permanently bonded" refers to the joining, adhering, connecting, attaching, or the like, of two elements of an article such that the elements tend to be and remain bonded during normal use conditions of the article.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the article.

"Stretch bonded" refers to an elastic member being bonded to another member while the elastic member is extended at least about 25 percent of its relaxed length. Desirably, the term "stretch bonded" refers to the situation wherein the elastic member is extended at least about 100 percent, and more desirably at least about 300 percent, of its relaxed length when it is bonded to the other member.

"Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

These terms may be defined with additional language in the remaining portions of the specification.

BRIEF DESCRIPTION OF THE DRAWINGS

Corresponding reference characters indicate corresponding parts throughout the drawings.

DETAILED DESCRIPTION OF THE PREFERRED EMBODIMENTS

Figure 1:
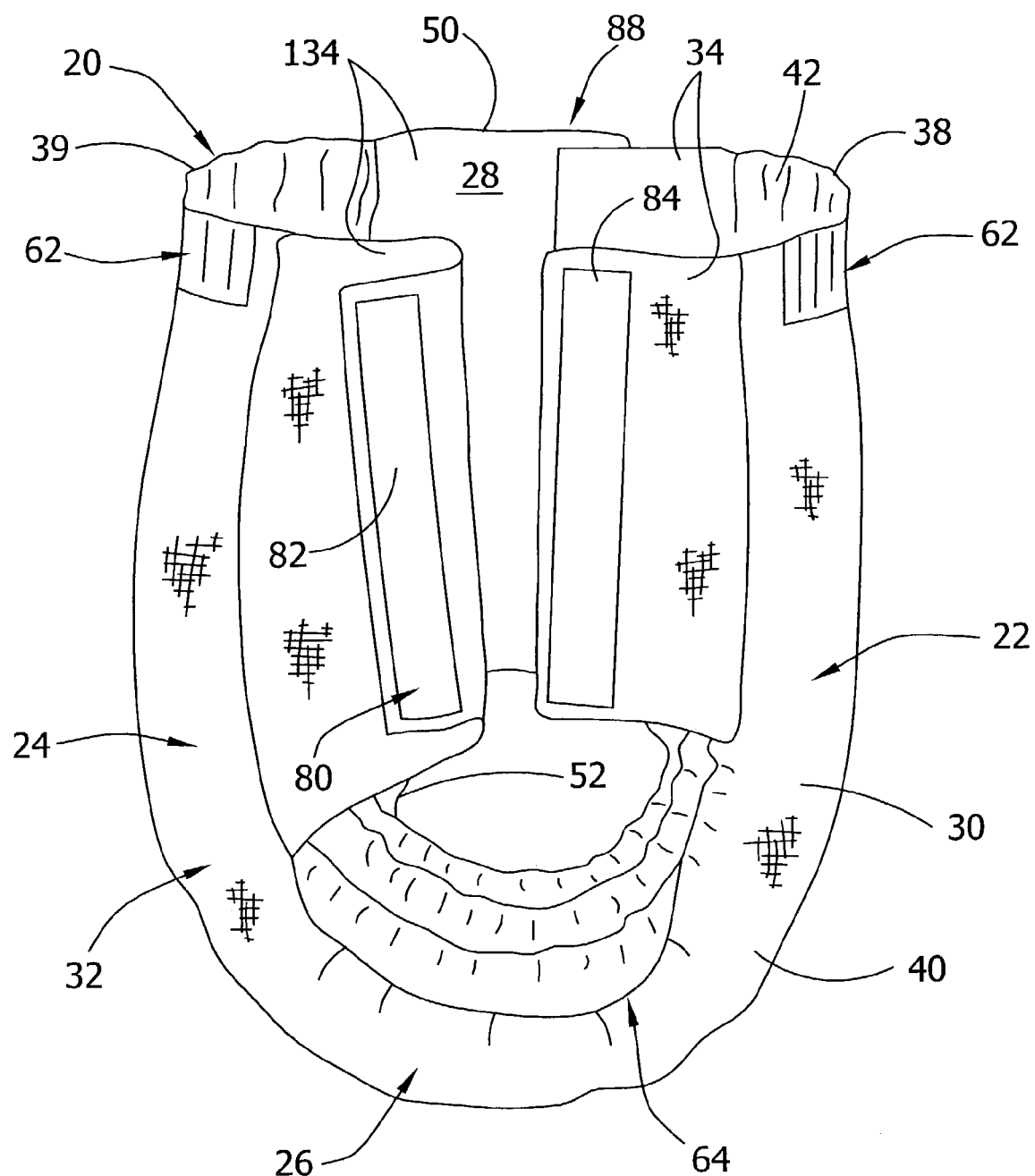
FIG. 1 is a side view of a pair of training pants with a mechanical fastening system of the pants shown fastened on one side of the training pants and unfastened on the other side of the training pants.

Referring now to the drawings and in particular to FIG. 1, an article in the form of children's toilet training pants is indicated in its entirety by the reference numeral 20 and incorporates a mechanical fastening system, generally indicated at 80, of the present invention for securing the pants in an assembled, three dimensional form. The article may or may not be absorbent, which generally refers to absorbent articles that may be placed against or in proximity to the body of the wearer to absorb and/or retain various liquid waste discharged from the body. The article may or may not also be disposable, which refers to articles that are intended to be discarded after a limited period of use instead of being laundered or otherwise restored for reuse. While the apparatus and methods of the present invention are shown and described herein in connection with children's toilet training pants, it is understood that the apparatus and methods may be used to make various other articles such as diapers, feminine hygiene products, incontinence products, medical articles such as medical garments, surgical pads and bandages, other personal care or health care garments, swim pants, athletic clothing, pants and shorts, and the like without departing from the scope of the present invention. As used herein, the term article is contemplated to also include discrete or continuous webs of material including, but not limited to, wipes, towels, napkins and other material webs.

By way of illustration only, various materials and methods for constructing the training pants 20 are disclosed in PCT Patent Application WO 00/37009 published Jun. 29, 2000 by A. Fletcher et al; U.S. Pat. No. 4,940,464 issued Jul. 10, 1990 to Van Gompel et al.; and U.S. Pat. No. 5,766,389 issued Jun. 16, 1998 to Brandon et al., which are incorporated herein by reference.

The pair of training pants 20 is illustrated in FIG. 1 in a partially fastened condition and comprises a front waist region 22, a back waist region 24, a crotch region 26 interconnecting the front and back waist regions, an inner surface 28 configured for contiguous relationship with the wearer, and an outer surface 30 opposite the inner surface. With additional reference to FIGS. 2 and 3, the training pants 20 also has a pair of laterally opposite side edges 36 and a pair of longitudinally opposite waist edges, respectively designated front waist edge 38 and back waist edge 39. The front waist region 22 is contiguous with the front waist edge 38, and the back waist region 24 is contiguous with the back waist edge 39.

Figure 2:
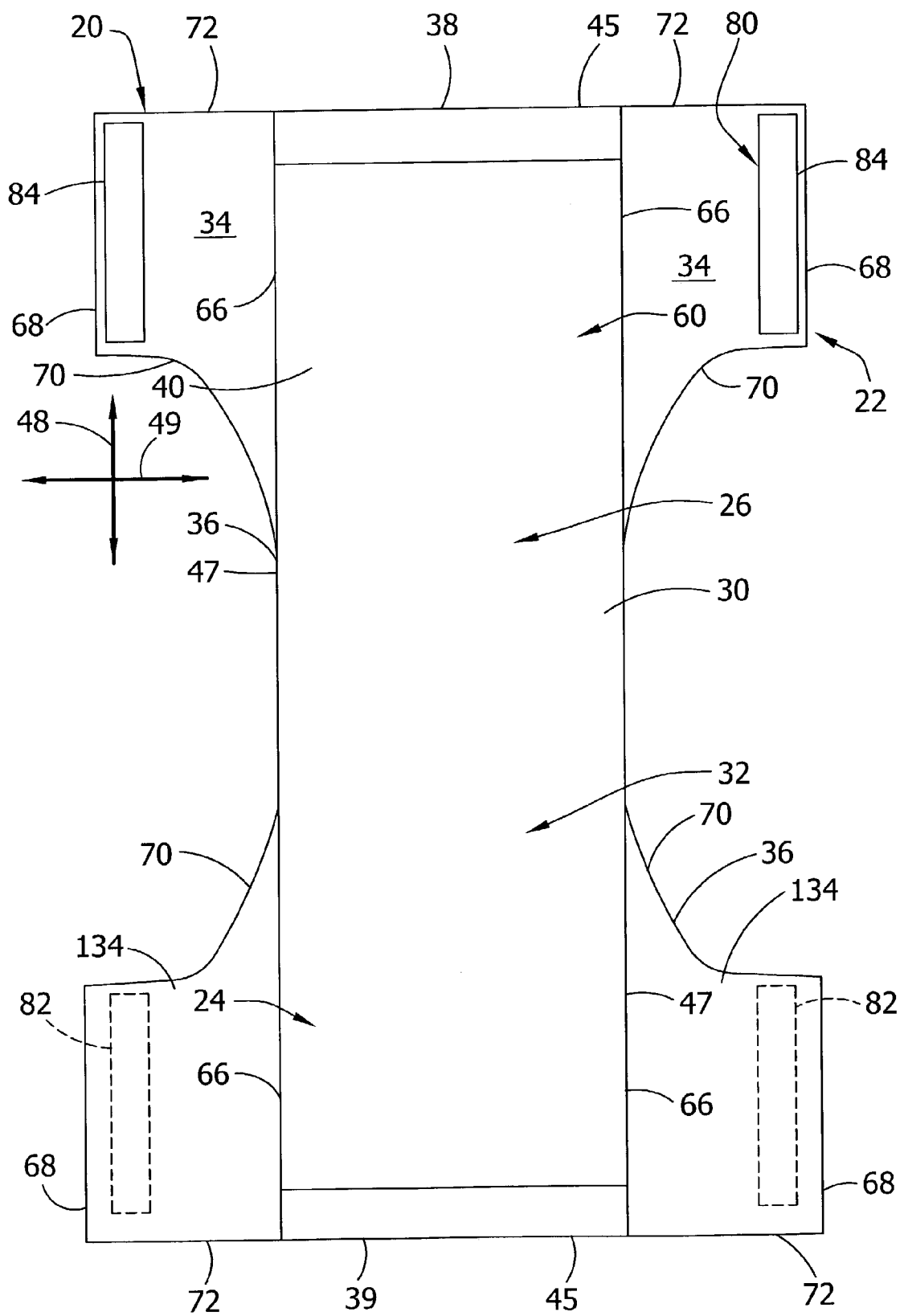
FIG. 2 is a plan view of the training pants of FIG. 1 in an unfastened, stretched and laid flat condition, and showing the surface of the training pants that faces away from the wearer.
Figure 3:
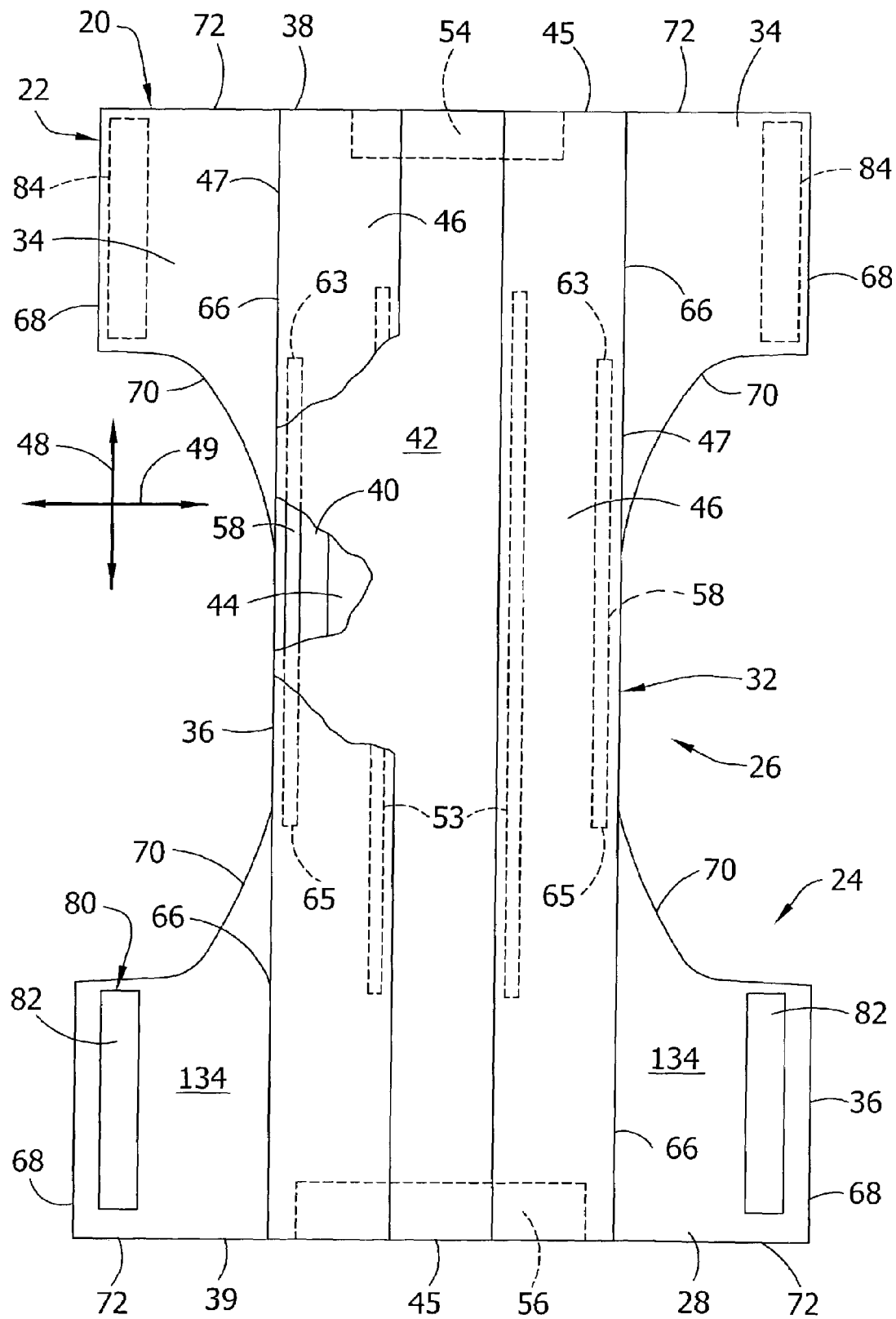
FIG. 3 is a plan view similar to FIG. 2, but showing the surface of the training pants that faces the wearer when worn, and with portions cut away to show underlying features.

The illustrated pants 20 comprises a central absorbent assembly, generally indicated at 32, which when laid flat can be rectangular or any other desired shape, a pair of laterally opposite front side panels 34 extending outward therefrom at the front waist region and a pair of laterally opposite back side panels 134 extending outward therefrom at the back waist region. The absorbent assembly 32 and side panels 34, 134 may comprise two or more separate elements, as shown in FIG. 1, or be integrally formed. The central absorbent assembly 32 of the illustrated embodiment comprises an outer cover 40, a bodyside liner 42 (FIGS. 1 and 3) connected to the outer cover in a superposed relation, an absorbent body 44 (FIG. 3) disposed between the outer cover and the bodyside liner, and a pair of containment flaps 46 (FIG. 3). The central absorbent assembly also has opposite ends 45 which form portions of the front and back waist edges 38 and 39, and opposite side edges 47 which form portions of the side edges 36 of the training pants 20 (FIGS. 2 and 3). Integrally formed side panels 34, 134 and absorbent assembly 32 would comprise at least some common materials, such as the bodyside liner, flap composite, outer cover, other materials and/or combinations thereof, and could define a one-piece elastic, stretchable, or nonstretchable pants. For further reference, arrows 48 and 49 depict the orientation of the longitudinal axis and the transverse or lateral axis, respectively, of the training pants 20.

With the training pants 20 in the fastened position as partially illustrated in FIG. 1, the front and back side panels 34, 134 are connected together by a fastening system 80 to define a three-dimensional pants configuration having a waist opening 50 and a pair of leg openings 52. The front waist region 22 comprises the portion of the training pants 20 which, when worn, is positioned on the front of the wearer while the back waist region 24 comprises the portion of the training pants which is positioned on the back of the wearer. The crotch region 26 of the training pants 20 comprises the portion of the training pants 20 which is positioned between the legs of the wearer and covers the lower torso of the wearer. The front and back side panels 34 and 134 comprise the portions of the training pants 20 which, when worn, are positioned on the hips of the wearer. The waist edges 38 and 39 of the training pants 20 are configured to encircle the waist of the wearer and together define the waist opening 50 (FIG. 1). Portions of the side edges 36 in the crotch region 26 generally define the leg openings 52.

The central absorbent assembly 32 is configured to contain and/or absorb exudates discharged from the wearer. For example, the containment flaps 46 are configured to provide a barrier to the transverse flow of body exudates. A flap elastic member 53 (FIG. 3) can be operatively joined with each containment flap 46 in any suitable manner as is well known in the art. The elasticized containment flaps 46 define a partially unattached edge which assumes an upright configuration in at least the crotch region 26 of the training pants 20 to form a seal against the wearer's body. The containment flaps 46 can be located along the side edges 36 of the pants 20, and can extend longitudinally along the entire length of the absorbent assembly 32 or may only extend partially along the length of the absorbent assembly. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pants 20 also suitably includes a front waist elastic member 54 (FIG. 3), a rear waist elastic member 56, and leg elastic members 58, as are known to those skilled in the art. The waist elastic members 54 and 56 can be operatively joined to the outer cover 40 and/or the bodyside liner 42 along the opposite waist edges 38 and 39, and can extend over part or all of the waist edges. The leg elastic members 58 can be operatively joined to the outer cover 40 and/or the bodyside liner 42 along the opposite side edges 36 and positioned in the crotch region 26 of the training pants 20. The leg elastic members 58 can be longitudinally aligned along each side edge 47 of the absorbent assembly 32. Each leg elastic member 58 has a front terminal point 63 and a back terminal point 65, which represent the longitudinal ends of the elastic gathering caused by the leg elastic members.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one particular embodiment, for example, the leg elastic members 58 comprise a plurality of dry-spun coalesced multifilament spandex elastomeric threads sold under the trade name LYCRA® and available from E. I. Du Pont de Nemours and Company, Wilmington, Del. U.S.A.

The outer cover 40 desirably comprises a material which is substantially liquid impermeable, and can be elastic, stretchable or nonstretchable. The outer cover 40 can be a single layer of liquid impermeable material, but desirably comprises a multi-layered laminate structure in which at least one of the layers is liquid impermeable. For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J. U.S.A. The liquid permeable outer layer can be any suitable material and is desirably one that provides a generally cloth-like texture. One example of such a material is a 20 gsm (grams per square meter) spunbond polypropylene nonwoven web. The outer layer may also be made of those materials of which the liquid permeable bodyside liner 42 is made. While it is not a necessity for the outer layer to be liquid permeable, it is desired that it provides a relatively cloth-like texture to the wearer.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Pliant Corporation of Schaumburg, Ill., U.S.A.

If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn. U.S.A. The outer cover 40 may also include appearance related components (not shown) as are well known in the art.

The liquid permeable bodyside liner 42 is illustrated as overlying the outer cover 40 and absorbent body 44, and may but need not have the same dimensions as the outer cover 40. The bodyside liner 42 is desirably compliant, soft feeling, and non-irritating to the child's skin. Further, the bodyside liner 42 can be less hydrophilic than the absorbent body 44, to present a relatively dry surface to the wearer and permit liquid to readily penetrate through its thickness. Alternatively, the bodyside liner 42 can be more hydrophilic or can have essentially the same affinity for moisture as the absorbent body 44 to present a relatively wet surface to the wearer to increase the sensation of being wet. This wet sensation can be useful as a training aid. The hydrophilic/hydrophobic properties can be varied across the length, width and depth of the bodyside liner 42 and absorbent body 44 to achieve the desired wetness sensation or leakage performance.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture comprising Ahcovel N-62 from Hodgson Textile Chemicals of Mount Holly, N.C., U.S.A. and Glucopan 220UP from Henkel Corporation of Ambler, Pa. in an active ratio of 3:1. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal center line.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. The outer cover 40, bodyside liner 42 and other materials used to construct the pants 20 can comprise elastomeric or nonelastomeric materials.

The absorbent body 44 (FIG. 3) is positioned between the outer cover 40 and the bodyside liner 42, which can be joined together by any suitable means such as adhesives, ultrasonic bonds, thermal bonds, or the like. The absorbent body 44 can be any structure which is generally compressible, conformable, non-irritating to the child's skin, and capable of absorbing and retaining liquids and certain body wastes, and may be manufactured in a wide variety of sizes and shapes, and from a wide variety of liquid absorbent materials commonly used in the art. For example, the absorbent body 44 can suitably comprise a matrix of hydrophilic fibers, such as a web of cellulosic fluff, mixed with particles of a high-absorbency material commonly known as superabsorbent material. In a particular embodiment, the absorbent body 44 comprises a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be non-uniformly mixed. The fluff and superabsorbent particles can also be selectively placed into desired zones of the absorbent body 44 to better contain and absorb body exudates. The concentration of the superabsorbent particles can also vary through the thickness of the absorbent body 44. Alternatively, the absorbent body 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 10 times its weight in water, and suitably is capable of absorbing more than about 25 times its weight in water.

In one embodiment, the absorbent body 44 comprises a blend of wood pulp fluff and superabsorbent material. One preferred type of pulp is identified with the trade designation CR1654, available from U.S. Alliance, Childersburg, Ala., U.S.A., and is a bleached, highly absorbent sulfate wood pulp containing primarily soft wood fibers and about 16 percent hardwood fibers. As a general rule, the superabsorbent material is present in the absorbent body 44 in an amount of from 0 to about 90 weight percent based on total weight of the absorbent assembly. The absorbent body 44 suitably has a density within the range of about 0.10 to about 0.35 grams per cubic centimeter. The absorbent body 44 may or may not be wrapped or encompassed by a suitable tissue wrap that may help maintain the integrity and/or shape of the absorbent assembly.

The central absorbent assembly 32 can also incorporate other materials or components designed primarily to receive, temporarily store, and/or transport liquid along the mutually facing surface with the absorbent body 44, thereby maximizing the absorbent capacity of the absorbent assembly. One suitable additional component is commonly referred to as a surge layer (not shown) and comprises a material having a basis weight of about 50 to about 120 grams per square meter, and more particularly comprises a through-air-bonded-carded web of a homogenous blend of 60 percent 3 denier type T-256 bicomponent fiber comprising a polyester core/polyethylene sheath and 40 percent 6 denier type T-295 polyester fiber, both commercially available from Kosa Corporation of Salisbury, N.C., U.S.A.

As noted previously, the illustrated training pants 20 have front and back side panels 34 and 134 disposed on each side of the absorbent assembly 32. The side panels 34, 134 can be permanently bonded along seams 66 to the central absorbent assembly 32 in the respective front and back waist regions 22 and 24. More particularly, as seen best in FIGS. 2 and 3, the front side panels 34 can be permanently bonded to and extend transversely outward beyond the side edges 47 of the absorbent assembly 32 in the front waist region 22, and the back side panels 134 can be permanently bonded to and extend transversely outward beyond the side edges of the absorbent assembly in the back waist region 24. The side panels 34 and 134 may be bonded to the absorbent assembly 32 using attachment means known to those skilled in the art such as adhesive, thermal or ultrasonic bonding. Alternatively, the side panels 34 and 134 can be formed as an integral portion of a component of the absorbent assembly 32. For example, the side panels can comprise a generally wider portion of the outer cover 40, the bodyside liner 42, and/or another component of the absorbent assembly 32. The front and back side panels 34 and 134 can be permanently bonded together or be releasably connected with one another such as by the fastening system 80 of the illustrated embodiment.

The front and back side panels 34, 134 each have an outer edge 68 spaced laterally from the seam 66, a leg end edge 70 disposed toward the longitudinal center of the training pants 20, and a waist end edge 72 disposed toward a longitudinal end of the training pants. The leg end edge 70 and waist end edge 72 extend from the side edges 47 of the absorbent assembly 32 to the outer edges 68. The leg end edges 70 of the side panels 34 and 134 form part of the side edges 36 of the training pants 20. The leg end edges 70 of the illustrated embodiment are suitably curved and/or angled relative to the transverse axis 49 to provide a better fit around the wearer's legs. However, it is understood that only one of the leg end edges 70 may be curved or angled, such as the leg end edge of the back waist region 24, or neither of the leg end edges may be curved or angled, without departing from the scope of this invention. The waist end edges 72 are suitably parallel to the transverse axis 49. The waist end edges 72 of the front side panels 34 form part of the front waist edge 38 of the training pants 20, and the waist end edges 72 of the back side panels 134 form part of the back waist edge 39 of the pants.

The side panels 34, 134 suitably, although not necessarily, comprise an elastic material capable of stretching in a direction generally parallel to the transverse axis 49 of the training pants 20. Suitable elastic materials, as well as one process of incorporating elastic side panels into training pants, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material may comprise a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference. Alternatively, the side panel material may comprise other woven or nonwoven materials, such as those described above as being suitable for the outer cover 40 or bodyside liner 42; mechanically pre-strained composites; or stretchable but inelastic materials.

The fastening system 80 comprises laterally opposite first fastening components 82 adapted for refastenable engagement to corresponding second fastening components 84. In one embodiment, a front or outer surface of each of the fastening components 82, 84 comprises a plurality of engaging elements. The engaging elements of the first fastening components 82 are adapted to repeatedly engage and disengage corresponding engaging elements of the second fastening components 84 to releasably secure the pants 20 in its three-dimensional configuration.

The fastening components 82, 84 can comprise any refastenable fasteners suitable for absorbent articles, such as adhesive fasteners, cohesive fasteners, mechanical fasteners, or the like. In particular embodiments the fastening components comprise mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated embodiment, the first fastening components 82 comprise loop fasteners and the second fastening components 84 comprise complementary hook fasteners. Alternatively, the first fastening components 82 may comprise hook fasteners and the second fastening components 84 may comprise complementary loop fasteners. In another embodiment, the fastening components 82, 84 can comprise interlocking similar surface fasteners, or adhesive and cohesive fastening elements such as an adhesive fastener and an adhesive-receptive landing zone or material; or the like. Although the training pants 20 illustrated in FIG. 1 show the back side panels 134 overlapping the front side panels 34 upon connection thereto, which is convenient, the training pants 20 can also be configured so that the front side panels overlap the back side panels when connected. One skilled in the art will recognize that the shape, density and polymer composition of the hooks and loops may be selected to obtain the desired level of engagement between the fastening components 82, 84. A more aggressive hook material may comprise a material with a greater average hook height and/or a greater percentage of directionally-aligned hooks.

Loop fasteners typically comprise a fabric or material including a plurality of loop members. The loop material can be formed of any suitable material, such as acrylic, polyamide, polyethylene, polypropylene or polyester, and can be formed by methods such as warp knitting, stitch bonding or needle punching. Loop materials can also comprise any fibrous structure capable of entangling or catching hook materials, such as carded, spunbonded or other nonwoven webs or composites, including elastomeric and nonelastomeric composites. Suitable loop materials are available from Guilford Mills, Inc., Greensboro, N.C., U.S.A. under the trade designation No. 36549. Another suitable loop material can comprise a pattern un-bonded web as disclosed in co-assigned U.S. Pat. No. 5,858,515 issued Jan. 12, 1999 to Stokes et al. incorporated herein by reference. The loop material may be secured to a base, or backing structure and the composite then secured to the pants 20, or the loop material may be secured directly to the pants so that the pair of pants serves as a backing for the loop material, or the loop material may be formed integrally with the pants, such as by constructing one or more layers or surfaces of the back side panels 134 from a loop material.

Hook fasteners typically comprise a fabric or material having a base or backing structure and a plurality of hook members extending upwardly from at least one surface of the backing structure. It should be understood that the term "hook" as used in reference to the hook members is non-limiting in the sense that the engaging elements of the hook fasteners may comprise shapes such as hooks, "T's", "mushrooms" or any other shape so long as they are adapted to releasably engage the loop fasteners so as to provide a secure, but non-destructively releasable engagement. In contrast to the loop fasteners which suitably comprise a flexible fabric, the hook material may advantageously comprise a resilient material to minimize unintentional disengagement of the fastening components 82, 84 as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material.

Suitable hook material can be molded or extruded from nylon, polypropylene, polyethylene or another suitable material. Suitable single-sided hook materials for the fastening components are available from commercial vendors such as Velcro Industries B.V., Amsterdam, Netherlands or affiliates thereof, identified as Velcro HTH-829, which has a thickness of about 0.9 millimeters (35 mils) and HTH-851, which has a thickness of about 0.5 millimeters (20 mils); and Minnesota Mining & Manufacturing Co., St. Paul, Minn. U.S.A., including specific materials identified as CS-600. As with the loop fastener, it is understood that the hook material may formed integrally with the pants 20, and more particularly with the side panels 34, without departing from the scope of this invention.

With particular reference to FIG. 3, the first fastening components 82 (e.g., the loop fasteners) are disposed on the inner surface 28 of the back side panels 134, and are suitably positioned adjacent the outer edges 68 of the back side panels 134. The second fastening components 84 (e.g., the hook fasteners) are disposed on the outer surface 30 of the front side panels 34 adjacent the outer edges 68 thereof as shown in FIG. 2, and are suitably sized to receive the first fastening components 82.

It is understood that the fastening components 82, 84 may also extend laterally out beyond the outer edges 68 of the side panels 134, 34. Where the first fastening components 82 comprise loop fasteners disposed on the inner surface 28 and the second fastening components 84 comprise hook fasteners disposed on the outer surface 30, the first fastening components can be sized larger than the second fastening components to ensure coverage of the rigid, outwardly-directed hooks.

The fastening components 82, 84 of the illustrated embodiments are rectangular, although they may alternatively be square, round, oval, curved or other suitable shapes. In particular embodiments, each of the fastening components 82, 84 has a length aligned generally parallel to the longitudinal axis 48 of the training pants 20 and a width aligned generally parallel to the transverse axis 49 of the training pants. For a child of about 9 to about 15 kilograms (20–30 pounds), for example, the length of the fastening components 82, 84 is desirably from about 50 to about 130 mm, such as about 100 mm, and the width is desirably from about 5 to about 30 mm, such as about 10 mm. In particular embodiments, the fastening components 82, 84 can have a length-to-width ratio of about 2 or greater, such as about 2 to about 25, and more particularly about 5 or greater, such as about 5 to about 8. For other embodiments such as for adult products, it may be desirable for one or more of the fastening components to comprise a plurality of relatively smaller fastening elements. In that case, a fastening component or individual fastening elements may have an even smaller length-to-width ratio, for example, of about 2 or less, and even about 1 or less.

The fastening components 84, 82 are suitably secured to the respective side panels 34, 134 by mechanical bonding. As used herein, mechanical bonding refers to non-adhesive bonding, such as by the application of pressure, ultrasonic energy, heat, laser energy or any other suitable form of energy which joins the fastening components to the side panels. It is understood that the fastening components 84, 82 may be adhered, such as by adhesive or cohesive means, to the respective side panels 34, 134 in addition to being mechanically bonded thereto, or the fastening components may only be mechanically bonded to the side panels, without departing from the scope of this invention. Where a fastening component 82, 84 is formed integrally with the respective side panel 134, 34, mechanical bonding may be omitted or may comprise mechanically bonding the fastener material layer of the side panel to one more other layers or surfaces of the side panel.

As shown in FIG. 1, when the fastening components 82, 84 are releasably engaged, the side edges 36 of the training pants 20 in the crotch region 26 define the leg openings 52, and the waist edges 38 and 39 including the waist end edges 72 of the side panels 34, 134 define the waist opening 50. For improved formation of the leg openings 52, it can be desirable in some embodiments for the front side panels 34 to be longitudinally spaced from the back side panels 134 as shown in FIGS. 2 and 3. For example, the front side panels 34 can be longitudinally spaced from the back side panels 134 by a distance equal to about 20 percent or greater, particularly from about 20 to about 60 percent, and more particularly from about 35 to about 50 percent, of the overall length of the pants 20.

When engaged, the fastening components 82, 84 of the illustrated embodiment define refastenable engagement seams 88 (FIG. 1) which desirably although not necessarily extend substantially the entire distance between the waist opening 50 and the leg openings 52. More specifically, the engagement seams 88 can cover about 70 to 100 percent, and particularly about 85 to about 95 percent, of the distance between the waist opening 50 and each leg opening 52, which distance is measured parallel to the longitudinal axis 48. To construct the engagement seams 88 to extend substantially the entire distance between the waist and leg openings 50 and 52, the fastening components 82, 84 can be formed to cover about 70 to 100 percent, and more particularly about 85 to about 95 percent, of the distance between the waist end edge 70 and the leg end edge 72 of the side panels 34, 134. In other embodiments, the fastening components can comprise a plurality of smaller fastening elements (not shown) covering a smaller portion of the distance between the waist opening 50 and the leg openings 52, for example, about 20 to about 70 percent, but spaced apart to span a larger percentage of the distance between the waist opening and the leg openings.

For the engagement seams 88 to be located at the sides of the wearer, it can be particularly desirable for the transverse distance between the fastening components 82 of the back side panels 134 to be substantially equal to the transverse distance between the fastening components 84 of the front side panel 134. The transverse distance between each respective set of fastening components 82, 84 is measured parallel to the transverse axis 49 between the longitudinal center lines of the respective fastening components, measured with the side panels 34, 134 in an unstretched condition. Alternatively, the lateral spacing between the fastening components 82 may be greater or less than the lateral spacing between the fastening components 84. It is also contemplated that fastening components 82 (and/or the fastening components 84) may not be laterally opposite each other, or may be only partially laterally opposite each other, such as by being offset longitudinally.

Figure 4:
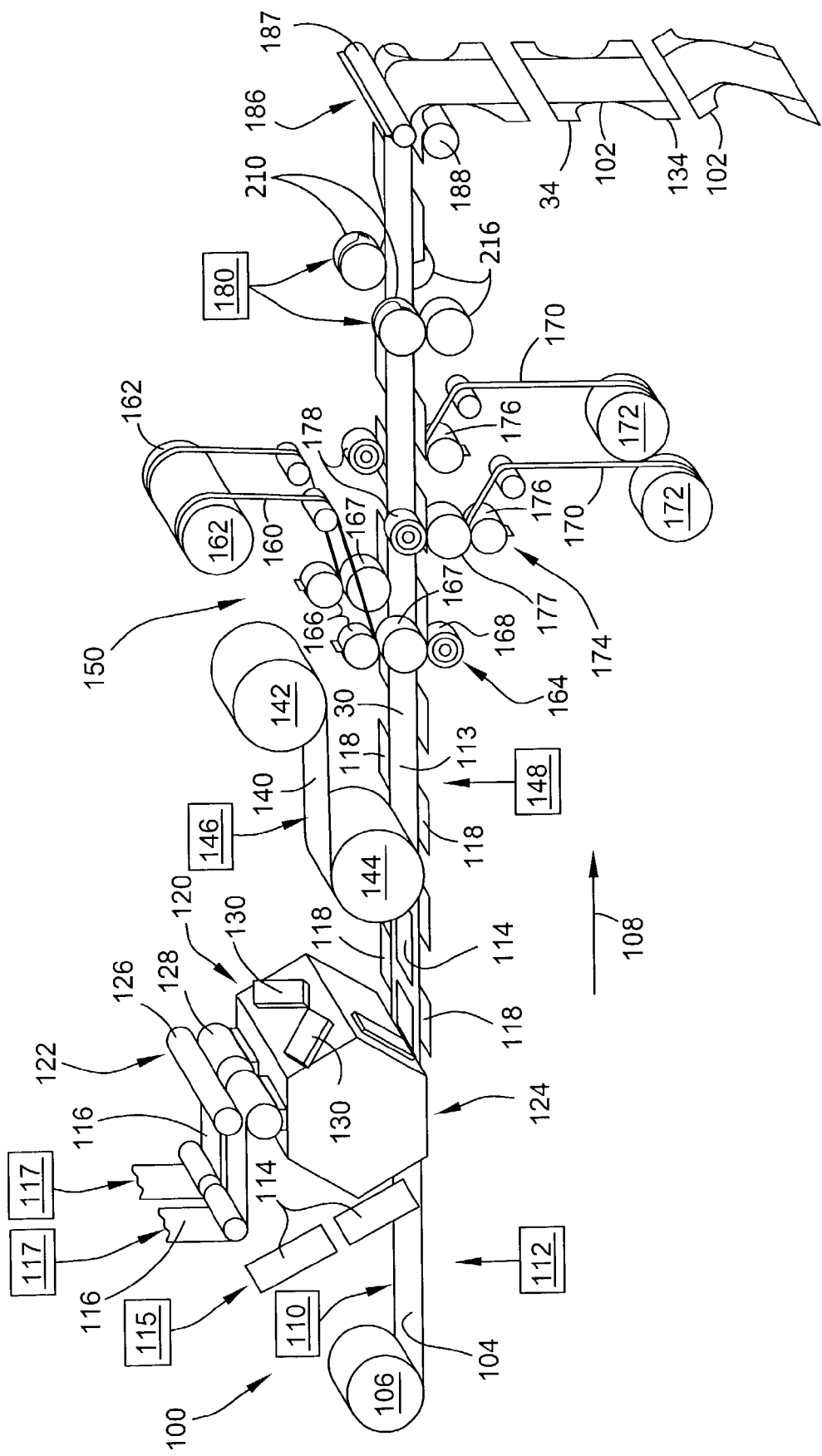
FIG. 4 is a schematic view of one embodiment of apparatus for making training pants according to the present invention.

FIG. 4 illustrates one embodiment of apparatus, generally indicated at 100, for making a continuous stream of partially assembled, discrete training pants 102. The method and apparatus described herein in relation to FIG. 4 is particularly suited to manufacture training pants 102 which are similar to the pants 20 illustrated in FIG. 1. However, it understood that the particular components of the apparatus 100 may vary depending on the specific type of absorbent article being manufactured.

The various components of the training pants 102 can be connected together by any means known to those skilled in the art such as, for example, adhesive, thermal and/or ultrasonic bonds. Desirably, most of the components are connected using ultrasonic bonding for improved manufacturing efficiency and reduced raw material costs. Certain article manufacturing equipment which is readily known and understood in the art, including frames and mounting structures, transport conveyors, transfer rolls, guide rolls, tension rolls, and the like, have not been shown in FIG. 4. Suitable absorbent supply mechanisms, web unwinds, conveyor systems, registration systems, drive systems, control systems and the like, for use with the present process are disclosed in U.S. Pat. No. 6,562,167 B2 issued May 13, 2003 to Coenen et al. and U.S. Pat. No. 5,766,389 issued Jun. 16, 1998 to Brandon et al., which are hereby incorporated herein by reference.

In the illustrated embodiment, a continuous supply of material 104 used to form the bodyside liner 42 of the pants 102 is provided from a supply source 106. The supply source 106 can comprise for example any standard unwind mechanism, which generally includes a pair of spindles, a festoon assembly, and a dancer roll for providing bodyside liner material 104 at a desired speed and tension.

Various components of the pants 20 can be disposed on and/or bonded to the bodyside liner material 104 as the material travels in a machine direction identified by arrow 108. In particular, a surge layer can be provided at an application station 110 and disposed on and/or bonded to the bodyside liner material 104. The surge layer can comprise either a continuous web or discrete sheets. Additionally, a containment flap module 112 can be provided downstream of the supply source 106 for attaching pre-assembled containment flaps to the bodyside liner material 104. As various components are added in the assembly section 100, a continuously moving product assemblage 113 is formed. The continuously moving product assemblage 113 defines a longitudinal center line 105 (FIG. 5) which can correspond to the machine center line. The product assemblage 113 will be cut downstream to form the partially assembled, discrete training pants 102.

Absorbent bodies 114 can be provided from a suitable supply source 115. The supply source 115 can be any conventional mechanism for supplying the absorbent bodies 114. Generally, a conventional supply source can include a hammermill for forming fluff fibers and, if desired, for providing an enclosure for mixing superabsorbent material with the fluff fibers, and then depositing the fluff and superabsorbent material on a forming drum having a desired absorbent design. The individual absorbent bodies 114 can be disposed intermittently on the continuously moving bodyside liner material 104, one for each pair of training pants. The position of the absorbent bodies 114 can be registered with the position of the surge layer, if employed. The absorbent bodies 114 can be bonded to one or more other components using adhesives or other suitable means. Alternatively, composite absorbent materials can be fed into the converting process from rolls or compressed packages, such as festooned bales.

Continuous webs of material 116 used to form the side panels 34 and 134 can be provided from suitable supply sources 117. The supply sources 117 can comprise one or more standard unwind mechanisms. The side panel material 116 can be cut into individual generally rectangular strips 118, also referred to as side panel strips 118, and positioned partially on the bodyside liner material 104 using an applicator device 120. In the cross machine direction, the individual strips 118 desirably extend laterally outward from the bodyside liner material 104 (see FIG. 5) and overlap the bodyside liner material by an amount such as about 2 cm or more to permit bonding of the strips to the bodyside liner and/or the containment flap material. In the machine direction 108, the position of the strips 118 can be registered relative to the absorbent bodies 114 so that the product assemblage 113 can be cut between the absorbent bodies with each strip 118 of side panel material 116 forming both a front side panel 34 and a back side panel 134 of consecutive articles 102.

One suitable applicator device 120 is disclosed in U.S. Pat. Nos. 5,104,116 issued Apr. 14, 1992 and U.S. Pat. No. 5,224,405 issued Jul. 6, 1993 both to Pohjola, which are incorporated herein by reference. The applicator device 120 can comprise a cutting assembly 122 and a rotatable transfer roll 124. The cutting assembly 122 employs a rotatable knife roll 126 and a rotatable vacuum anvil roll 128 to cut individual strips 118 from the continuous side panel material 116. The strips 118 cut by a blade on the knife roll 126 can be maintained on the anvil roll 128 by vacuum and transferred to the transfer roll 124.

The rotatable transfer roll 124 can comprise a plurality of rotatable vacuum pucks 130. The vacuum pucks 130 receive the strips 118 of material 116 from the cutting assembly 122 and rotate and transfer the strips to the continuously moving bodyside liner material 104. When the strips 118 are positioned as desired relative to the bodyside liner material 104, the strips are released from the pucks 130 by extinguishing the vacuum in the pucks. The pucks 130 then continue to rotate toward the cutting assembly 122 to receive other strips. The resulting product assemblage 113 thus has a plurality of pairs of transversely opposite side panel strips 118 whereby the side panel strips extend transversely outward from the longitudinal center line 105 of the product assemblage.

A continuous supply of material 140 used to form the outer cover 40 can be provided from a supply roll 142 or other suitable source. The outer cover material 140 can be transported over a laminator roll 144 and married with the bodyside liner material 104. The absorbent bodies 114 are thereby sandwiched between the continuous materials 104 and 140. The inward portions of the strips 118 of side panel material 116 can also be disposed between the bodyside liner material 104 and the outer cover material 140. Alternative configurations for attaching the side panel material 116 are disclosed by Van Gompel et al. Various components such as leg elastics 58 or waist elastics 54 and 56 can be bonded to the outer cover material 140 at an application station 146 prior to uniting the bodyside liner and outer cover materials 104, 140. Alternatively, leg elastics or waist elastics can be initially bonded to the bodyside liner material 104 or another material.

Bonding devices 148 such as ultrasonic bonding devices can be employed downstream of the laminator roll 144 to bond the bodyside liner material 104, side panel material 116 and outer cover material 140. For example, these materials can be transported between a conventional rotary ultrasonic horn and anvil roll. Suitable ultrasonic bonding devices are described in U.S. Pat. No. 5,110,403 to Ehlert, which is incorporated herein by reference. Alternatively, the ultrasonic horn may be a stationary ultrasonic horn as is also known to those skilled in the art. Other suitable ultrasonic horns and ultrasonic bonders are commercially available from Branson Sonic Power Company, Danbury, Conn U.S.A. The bonding devices 148 could otherwise be a thermal or adhesive bonder as are well known.

The continuously moving product assemblage 113 next advances to a fastener application station 150 where fastening components 82, 84 are positioned on and bonded to the strips 118 of side panel material 116. The location of the fastening components on the composite is a function in part of the configuration of the apparatus 100. The illustrated apparatus 100 is configured so that the upwardly facing major surface of the product assemblage 113 will become the outer surface 30 of the training pants 20 and the downwardly facing major surface will become the inner surface 28. Moreover, the illustrated apparatus 100 is configured to produce training pants 102 having the front waist region 22 of a leading pair of pants connected to the back waist region 24 of a trailing pair as shown in FIG. 5.

The process could alternatively employ any combination of different orientations. For example, the upwardly facing surface of the product assemblage 113 could form the inner surface 28 of finished articles. Additionally, or alternatively, the back waist region 24 of a leading pair of pants 102 can be connected to the front waist region 22 of the trailing pair of pants, or the pants can be arranged in a front-to-front/back-to-back relationship. Still alternatively, the apparatus 100 could be constructed as a cross-machine direction process wherein the longitudinal axis 48 of each pair of pants could be perpendicular to the machine direction 108 during part or all of the assembly process.

Figure 5:
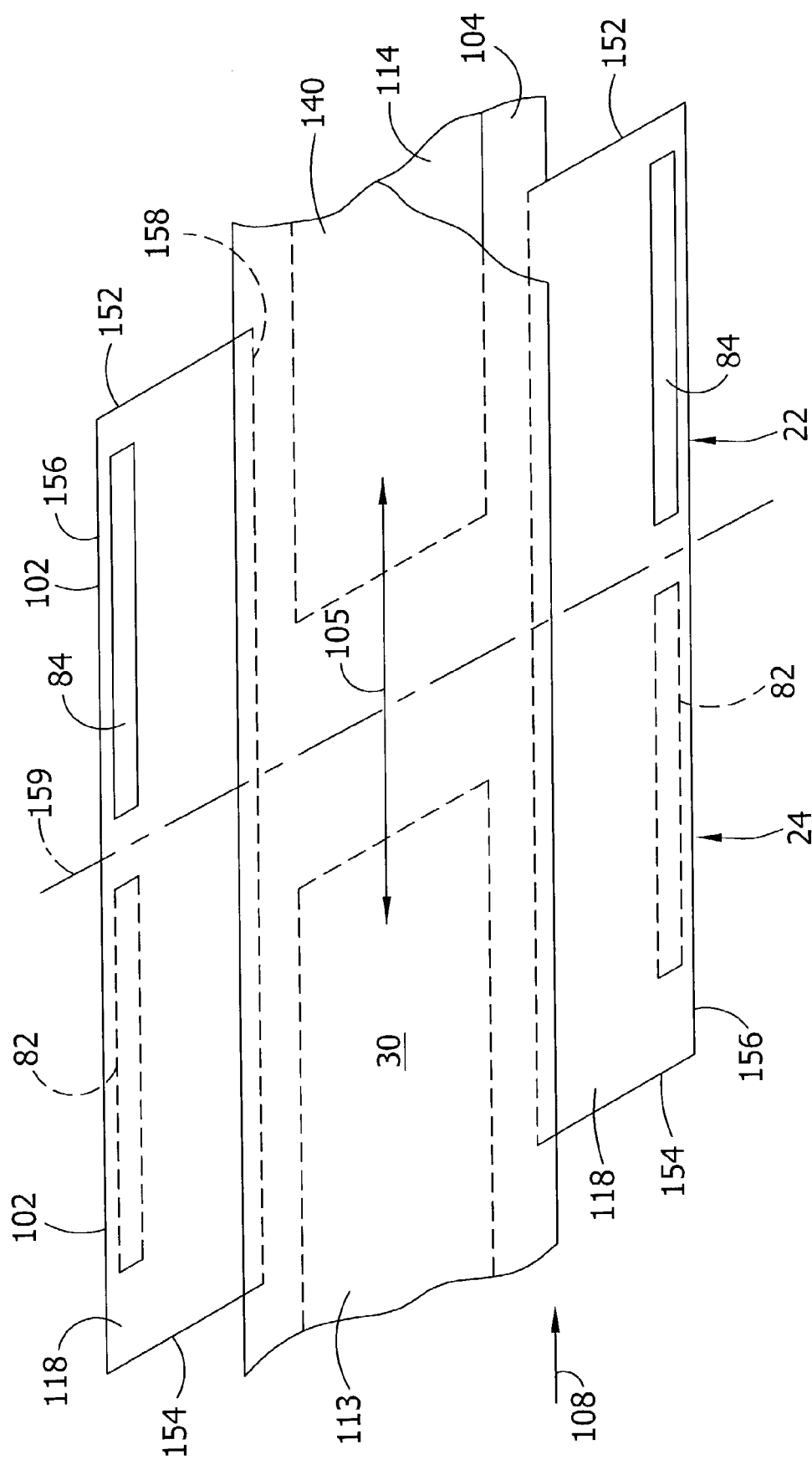
FIG. 5 is a portion of a product assemblage at one point in the process illustrated in FIG. 4.

The location of the fastening components 82, 84 in this embodiment is best illustrated in FIG. 5, which shows a portion of the product assemblage 113 moving in the direction of arrow 108 immediately following application of the fastening components 82, 84 to the product assemblage. Each individual strip 118 of side panel material 116 defines a leading edge 152, a trailing edge 154, a distal edge 156 and an interior edge 158. A dashed line 159 illustrates the location at which the product assemblage 113 can subsequently be cut to provide the discrete training pants 20. Based on the illustrated orientation of the continuously moving product assemblage 113, the first fastening components 82 can be positioned on and bonded to the underside of the strips 118 corresponding to the back side panels 134 and the second fastening components 84 can be positioned on and bonded to the top surface of the strips corresponding to the front side panels 34.

The first fastening components 82 are desirably disposed on opposite sides of the longitudinal center line 105 at selected cross machine direction locations, and the second fastening components 84 are desirably disposed on opposite sides of the longitudinal center line 105 at the same selected cross machine direction locations as the first fastening components 82. For purposes of the present invention, the term "cross machine direction location" refers to a location spaced from the machine center line, measured perpendicular thereto.

With reference again to FIG. 4, continuous webs of second fastener material 160 used to form the second fastening components 84 can be provided from supply rolls 162 or other suitable sources. The second fastener material 160 can be cut into individual second fastening components by cutting assemblies 164 or other suitable devices. The illustrated cutting assemblies 164 include rotatable knife rolls 166, rotatable vacuum anvil rolls 167, and rotatable backing rolls 168. The continuous second fastener materials 160 can be cut by blades on the knife rolls 166, maintained on the anvil rolls 167 by vacuum, and disposed on the top surfaces of the strips 118 of side panel material 116.

Similarly, continuous webs of first fastener material 170 used to form the first fastening components 82 can be provided from supply rolls 172 or other suitable sources. The first fastener material 170 can be cut into individual first fastening components 82 by cutting assemblies 174 or other suitable devices. The illustrated cutting assemblies 174 include rotatable knife rolls 176, rotatable vacuum anvil rolls 177, and rotatable backing rolls 178. The continuous first fastener material webs 170 can be cut by blades on the knife rolls 176, maintained on the anvil rolls 177 by vacuum, and disposed on the undersides of the strips 118 of side panel material 116.

With the fastening components 82, 84 positioned on the side panel strips 118, the product assemblage 113 is further transported in the machine direction past apparatus, generally indicated at 180, of the present invention for mechanically bonding and cutting the pants 102 of the assemblage, and more particularly to mechanically bond the first fastener material 170 and the second fastener material 160 to the side panel strips 118, and for cutting away portions of the side panel strips 118 to provide the angled and/or curved leg end edges 70 of the front and back side panels 34, 134 of the pants. The apparatus 180 are transversely spaced from each other on opposite sides of the longitudinal centerline 105 to mechanically bond and cut the side panels 34, 134 extending outward from each side edge 47 of the central absorbent assembly 32. The fastening components 82, 84 can be maintained on the side panel strips 118 as the product assemblage 113 is transported to the mechanical bonding and cutting apparatus 180 using suitable vacuum devices (not shown), or they can be attached to the side panel strips at the fastener application station 150 with adhesive bonds.

Figure 6:
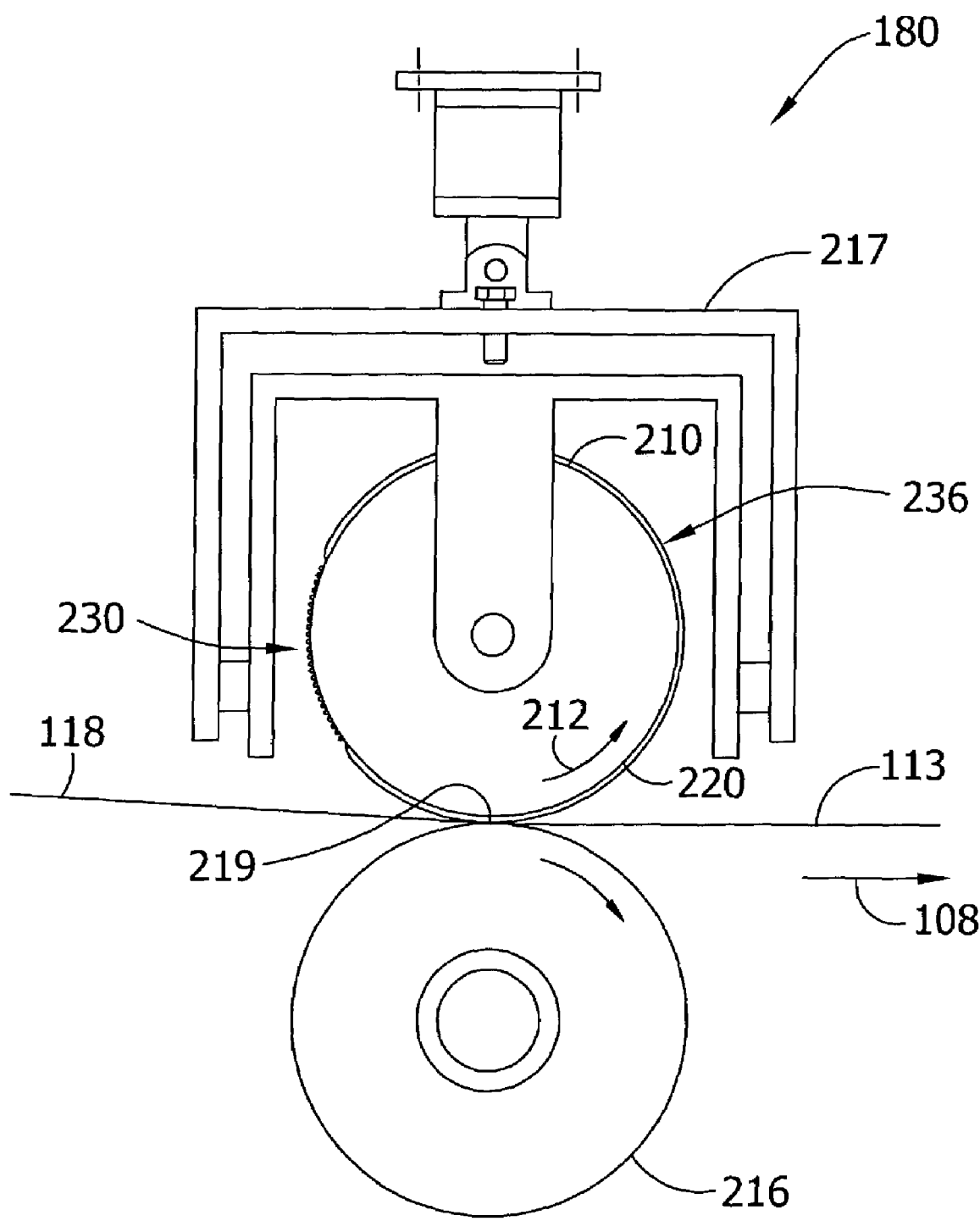
FIG. 6 is a schematic side elevation view of one embodiment of mechanical bonding and cutting apparatus of the present invention.

As shown in FIG. 6, each mechanical bonding and cutting apparatus 180 (only one of which is shown in FIG. 6, the other being of substantially the same construction) comprises an anvil roll 210 (broadly, a first member of the mechanical bonding and cutting apparatus) and a bonding roll 216 (broadly, a second member of the mechanical bonding and cutting apparatus) positioned in opposed, parallel relationship with the anvil roll to define a nip 219 therebetween. The anvil roll 210 is rotatably mounted on suitable support structure 217, such as by conventional bearings (not shown), for rotation about its rotation axis in the direction indicated by arrow 212 between a bonding mode in which the product assemblage 113 is subjected to mechanical bonding as it passes through the nip 219 and a cutting mode in which the product assemblage is subjected to a cutting operation as it passes through the nip. As is shown in FIG. 6, rotation of the anvil roll 210 in the direction indicated by arrow 212 corresponds to tangential movement of the anvil roll at the nip 219 generally in the machine direction 108 in which the product assemblage is transported.

It is understood that the anvil roll 210 and bonding roll 216 may be slightly spaced from each other at the nip throughout the full revolution of the anvil roll, or they may contact each other at the nip throughout all or part of a full revolution of the anvil roll.

In general, the anvil roll 210 may be made from any metal having suitable mechanical properties. For example, in one embodiment the anvil roll 210 is constructed of hardened steel. The width of the anvil roll 210 of the illustrated embodiment is suitably equal to or less than the transverse outward extension of the side panel strips 118 from the side edges 47 of the central absorbent assembly 32. As an example, the anvil roll 210 shown in FIG. 6 has a width of about 2.75 inches (about 7 cm). In this manner, mechanical bonding and cutting of the pants 102 of the assemblage 113 is limited to the side panel strips 118 thereof. However, it is understood that the anvil roll width may be smaller, or it may be larger so that upon transporting the product assemblage 113 in the machine direction 108, other (or additional) components of the product assemblage 113 pass through the nip 219 defined by the anvil roll 210 and bonding roll 216 without departing from the scope of this invention.

In one embodiment, the bonding roll 216 comprises a rotary ultrasonic horn (not shown). Representative examples of rotary ultrasonic horns which can be used are described in commonly assigned U.S. Pat. No. 5,096,532 to Neuwirth et al. and U.S. Pat. No. 5,110,403 to Ehlert, which are herein incorporated by reference. In general, the rotary ultrasonic horn may be made from any metal having suitable acoustical and mechanical properties. Suitable metals include aluminum, nickel alloys, nickel-copper alloys, titanium and some alloy steels. Alternatively, the ultrasonic horn may be a stationary ultrasonic horn as is also known to those skilled in the art. It is also contemplated that the second member of the mechanical bonding and cutting apparatus may be other than a bonding roll 216, such as a plate or other suitable structure forming a nip with the anvil roll 210, and remain within the scope of this invention.

The anvil roll 210 has a circumferential outer surface 220 configured for intermittent mechanical bonding of the fastener materials 160, 170 and the side panel strips 118 together and cutting of the side panel strips to form the desired leg end edge 70 configurations upon rotation of the anvil roll. As representatively illustrated in FIGS. 7 and 8, a circumferential segment of the outer surface 220 of the anvil roll 210 broadly defines a bonding segment, generally indicated at 230, thereof and comprises a plurality of projections 222 extending outward therefrom. The projections 222 of the illustrated embodiment are grouped within a generally rectangular region defining a width of the bonding segment 230 that is less than the width of the anvil roll outer surface 220, and more particularly corresponds generally to the width of the fastening components 160. 170 positioned on the side panel strips 118. However, it is understood that the width of the bonding segment 230 may be greater than or less than the width of the fastener components 160, 170. It is also contemplated that the width of the bonding segment 230 may be substantially equal to the width of the anvil roll outer surface 220 (e.g., the bonding segment may span the width of the anvil roll outer surface) without departing from the scope of this invention.

Figure 7:
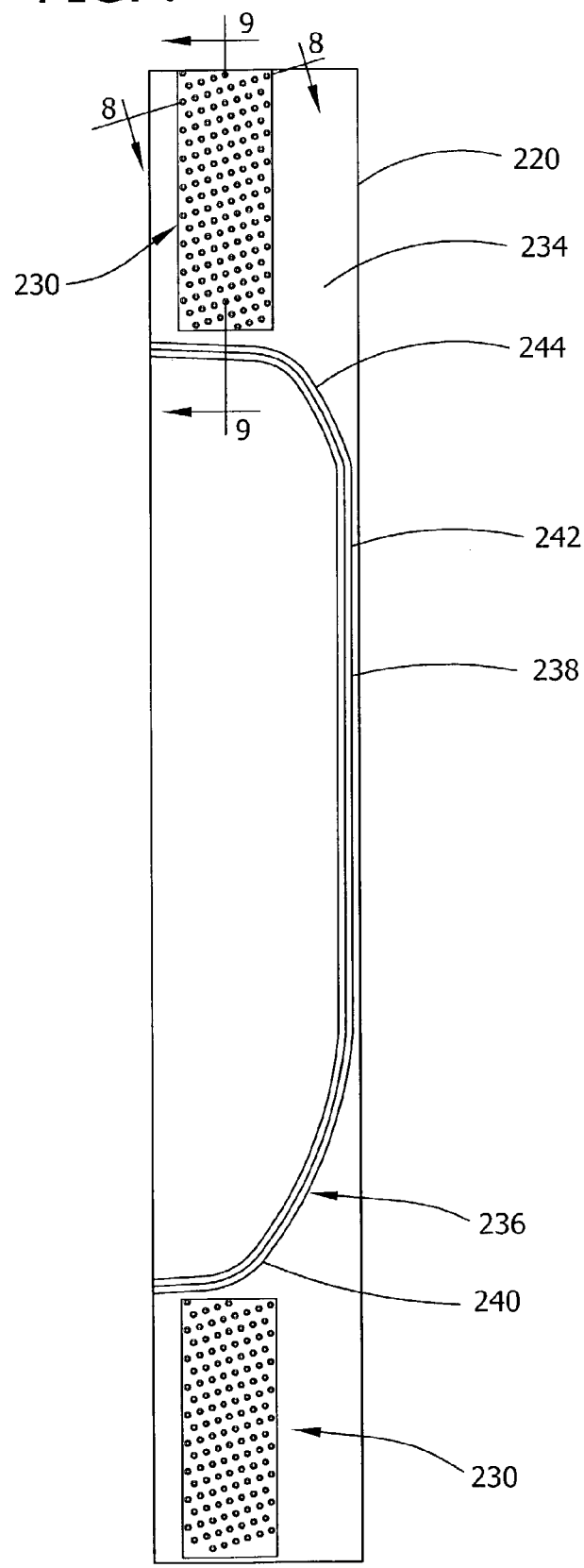
FIG. 7 is a flat view of a circumferential outer surface of an anvil roll of the mechanical bonding and cutting apparatus of FIG. 6.
Figure 10:
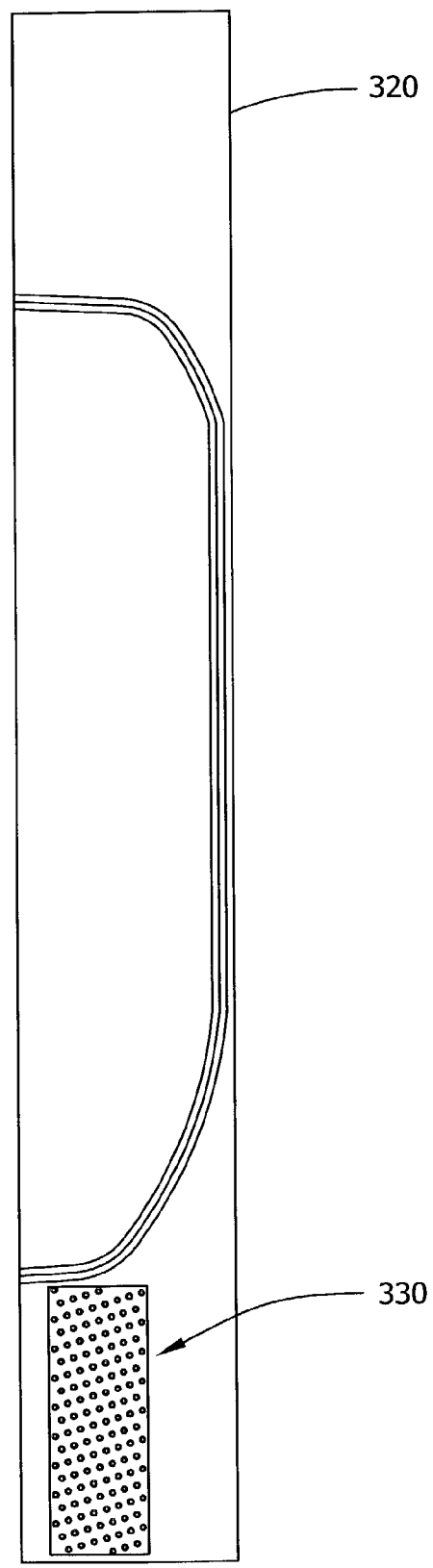
FIG. 10 is a flat view of an alternative embodiment of a circumferential outer surface of the anvil roll.

In the laid flat illustration of the anvil roll 210 in FIG. 7, the anvil roll outer surface 220 is bisected generally centrally of the continuous bonding segment 230 to correspond to the location (159 in FIG. 5) at which a trailing edge of one pair of the pants 102 of the assemblage 113 is connected to the leading edge of the next pair of pants. The length of the continuous bonding segment 230 is such that a portion (e.g., about one-half, or one end of the bisected bonding segment of FIG. 7) of the length of the bonding segment can be used for mechanically bonding the fastening component 84 to the side panel strip 118 corresponding to the front side panel 34 of one pair of pants 102 of the assemblage 113. The remaining length (e.g., the other end of the bisected bonding segment 230 of FIG. 7) of the bonding segment can be used for mechanically bonding the fastening component 82 to the side panel strip 118 corresponding to the back side panel 134 of a trailing pair of pants 102 of the assemblage 113. However, it is understood that the outer surface 220 of the anvil roll 210 may comprise two or more discrete (e.g. circumferentially and/or transversely spaced) bonding segments without departing from the scope of this invention. It is also contemplated that the bonding segment 230 may be sized for mechanically bonding only one fastening component 82, 84 to the side panel strip 118 as shown in FIG. 10 and described later herein.

Figure 8:
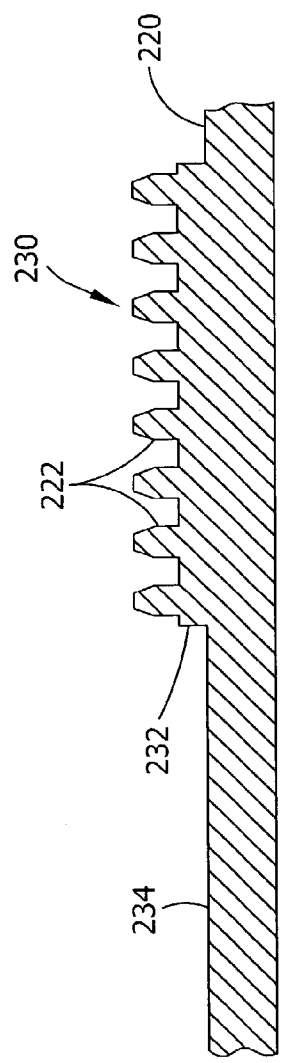
FIG. 8 is a fragmented cross-section taken in the plane of line 8—8 of FIG. 7.
Figure 9:
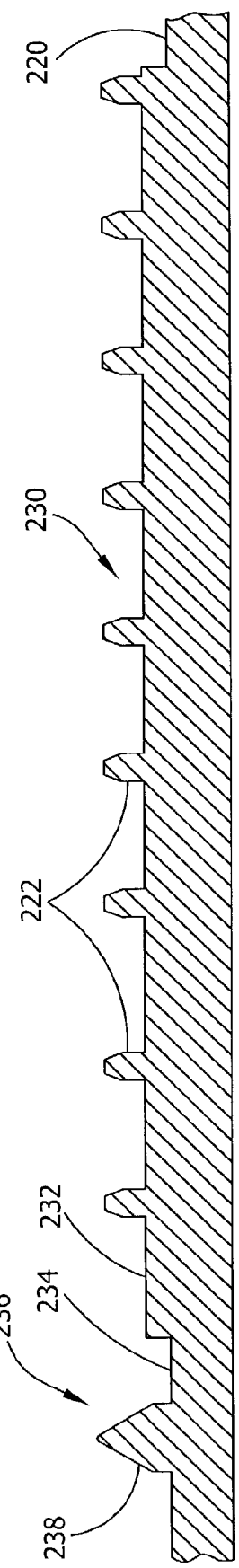
FIG. 9 is a fragmented cross-section taken in the plane of line 9—9 of FIG. 7.

The bonding segment projections 222 of the illustrated embodiment are generally circular pins having a diameter which tapers inward toward its outer tip. For example, the pins shown in FIGS. 8 and 9 each have a base diameter of about 0.86 inches (e.g., about 2.18 mm), and an outer tip diameter of about 0.48 inches (e.g., about 1.22 mm). However, the projections 222 can be sized in cross-section other than as set forth above, and/or they may have other cross-sectional shapes, such as square, S-shape, hexagon or other useful shapes. As is also shown in FIGS. 8 and 9, the pins are formed integrally with a platform 232 formed on the anvil roll outer surface whereby the platform extends radially outward beyond a reference outer surface 234 or reference outer diameter of the anvil roll. The pins extend outward from the platform 232 approximately 0.125 inches (e.g., about 3.175 mm). The platform height is approximately 0.0765 inches (e.g., about 1.943 mm) above (e.g., outward of) of the reference outer surface 234.

The projections 222 defining the bonding segment 230 mechanically bond the fastening components 160, 170 to the side panel strips 118 in a pattern of discrete bond points as the side panel strips pass through the nip 219 in the bonding mode of the apparatus. Alternatively, the bonding segment 230 of the anvil roll outer surface 220 may be defined by a plurality of depressions (not shown) disposed therein such that the mechanical bonding forms a continuous bond pattern on the side panel strips 118. The projections 222 may be arranged in any repeating or arbitrary pattern depending upon the desired bond pattern. Particular ultrasonic bond patterns comprising bonds which are compatible with the mechanical fastening of materials are disclosed in co-assigned U.S. Pat. No. 5,660,666 issued Aug. 26, 1997 to Dilnik at al., and commonly assigned U.S. Pat. No. 6,969,377 issued Nov. 29, 2005 to Koele, et al., both of which are incorporated herein by reference.

Still referring to FIGS. 6 and 7, the circumferential outer surface 220 of the anvil roll 210 further comprises a cutting segment, generally indicated at 236, for cutting the product assemblage, and more particularly for cutting the side panel strips 118, in the cutting mode of the apparatus. At least a portion of the cutting segment 236, and more suitably the full circumferential extent of the cutting segment, is discrete from the bonding segment 230, such as by being located at a different circumferential location of the anvil roll outer surface 220 than the bonding segment, so that in the bonding mode of the apparatus the anvil roll 210 is oriented such that the bonding segment of the outer surface defines the nip 219 together with the bonding roll 216 and the cutting segment is external of the nip and in the cutting mode of the apparatus the anvil roll is oriented such that the cutting segment 236 defines the nip together with the bonding roll and the bonding segment is external of the nip.

The cutting segment 236 of the illustrated embodiment comprises a blade 238 projecting outward of the anvil roll outer surface 220 and extending continuously along a portion of the circumference thereof. It is understood, however, that the cutting segment 236 may comprise a serrated blade or it may comprise two or more blades in closely spaced end-to-end relationship with each other, without departing from the scope of this invention. The blade 238 also extends transversely across the anvil roll outer surface 220 (e.g., transverse to the circumference of the anvil roll 210) for transversely cutting each pair of pants 102 of the product assemblage 113, and more particularly each of the side panel strips 118. For example, in the illustrated embodiment the blade 238 extends transversely across the entire width of the anvil roll outer surface 220. However, the blade 238 may extend transversely across only a portion of the width of the outer surface 220 of the anvil roll 210 without departing from the scope of this invention.

More particularly, the blade 238 of the cutting segment 236 shown in FIG. 7 extends both transversely and circumferentially on the anvil roll outer surface 220 generally along a first portion 240 of the cutting segment to define a first cutting pattern of the blade. The first cutting pattern is shaped to cut a portion of the side panel strip 118 to form the curved leg end edge 70 of the back side panel 134 of the completed training pants 102. A transition portion 242 of the cutting blade 238 extends from the first portion 240 thereof circumferentially on the anvil roll outer surface 220 to a second portion 244 of the cutting blade which extends transversely and circumferentially on the outer surface to define a second cutting pattern of the blade. The second cutting pattern is shaped to cut a portion of the sequentially next side panel strip 118 to form the curved leg end edge 70 of the front side panel 34 of the completed training pants 102.

Figure 11:
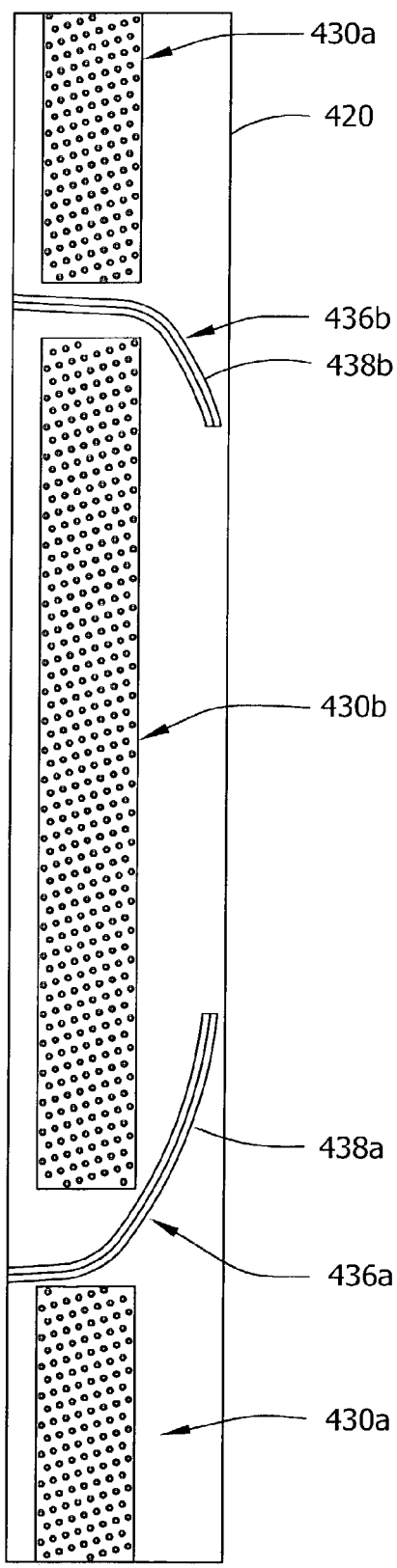
FIG. 11 is a flat view of another alternative embodiment of a circumferential outer surface of the anvil roll.

While the anvil roll outer surface 220 shown in FIG. 7 comprises a single cutting segment 236 configured to cut each of the side panel strips 118 corresponding respectively to the front and back side panels 34, 134 of the completed training pants 102, it is understood that the cutting segment may be configured for cutting only one of the side panel strips whereby the other side panel strip remains uncut as the assemblage 113 of training pants pass the mechanical bonding and cutting apparatus 180. It is also understood that the anvil roll outer surface 220 may comprise two or more discrete cutting segments as shown in FIG. 11 and described later herein.

As seen best in FIG. 9, the blade 238 is generally triangular in cross-section. However, it is understood that alternative cross-sectional shapes suitable for cutting material webs may be used. The blade 238 suitably projects outward of the anvil roll outer surface 220 (e.g., relative to the reference surface, or reference diameter) further than the outer ends of the projections 222 of the bonding segment 230. For example, the blade 238 of the illustrated embodiment projects outward of the reference surface, or reference diameter, approximately 0.2 inches (approximately 0.5 cm).

In the illustrated embodiment, the circumference of the anvil roll outer surface 220 (e.g., including the bonding and cutting segments 230, 236) is suitably sized to correspond generally to the length (e.g., along the longitudinal axis 48) of each pair of the training pants 102 of the product assemblage 113. For example, the length of the training pants 102 of the illustrated embodiment and the circumference of the anvil roll 210 can each be about 20 inches (about 50.8 mm). In such an arrangement, one revolution of the anvil roll 210 is intended to correspond to a single pair of training pants 102 passing through the nip 219 in the machine direction 108. However, the diameter and outer circumference of the anvil roll 210 may be sized for more than one revolution per pair of training pants 102, or it may be sized for less than one revolution per pair of training pants 102 (e.g., one revolution may correspond to two or more pair of training pants passing through the nip).

In operation, the assemblage 113 of training pants 102 is transported in the machine direction 108 to the mechanical bonding and cutting apparatus 180. As the leading edge (e.g., the waist end edge 72) of a pair of training pants 102 of the assemblage 113 passes the apparatus 180, the side panel strip 118 corresponding to the back side panel 134 of the completed pants enters the nip 219 between the anvil roll 210 and bonding roll 216. The side panel strip 118 (with the fastening component 170 thereon) enters the nip 219 with the anvil roll 210 in a rotational orientation corresponding to the bonding mode of the apparatus 180 in which the bonding segment 230 of the outer surface 220 of the anvil roll (and more particularly the mid-portion of the bonding segment 230 at which the anvil roll outer surface shown in FIG. 7 is bisected) defines the nip 219 together with the bonding roll 216. At least part of the cutting segment 236, and more suitably the entire cutting segment, is external of the nip 219. As the side panel strip 118 passes through the nip 219 in the bonding mode of the apparatus 180, the bonding segment 230 and bonding roll 216 facilitate mechanical bonding of the fastening component 170 to the side panel strip.

Upon further transport of the assemblage 113 in the machine direction 108 and upon further rotation of the anvil roll 210, the cutting segment 236 of the anvil roll outer surface 220 is rotated into a position corresponding to the cutting mode of the apparatus 180 in which the cutting segment, and more particularly the first portion 240 of the blade 238 defines the nip 219 together with the bonding roll 216 and the bonding segment 230 is external of the nip. As the trailing edge of the side panel strip 118 corresponding to the back side panel enters the nip 219, the blade 238 cuts a portion of the side panel strip to form the leg end edge 70 of the back side panel 124. The anvil roll 210 continues to rotate the rest of the cutting segment 236 through the nip 219 so that upon further transport of the assemblage 113 in the machine direction 108, a portion of the leading edge of the side panel strip 118 corresponding to the front side panel 32 is cut by the second portion 244 to form the leg end edge 70 of the front side panel. Cut material is removed from the side panel strip 118 by allowing it to simply fall away from the strip 118 or by using a conventional trim removal technique such as vacuum and/or other suitable techniques.

The anvil roll 210 further rotates to a position and orientation in which the bonding segment 230 again defines the nip 219 together with the bonding roll 216 as the remainder of the side panel strip 118 corresponding to the front side panel 34 (along with the fastening component 160 thereon) passes through the nip 219. The fastening component 160 and side panel strip 118 are thus mechanically bonded together. The leading edge of the next pair of training pants 102 of the product assemblage then passes into the nip 219 as the anvil roll 210 completes an entire revolution, with the bonding segment 230 still defining the nip.

While the mechanical bonding and cutting apparatus 180 is shown in the drawings and described herein as comprising two separate anvil rolls 210 spaced transversly from each other according to the spacing between the side panel strips 118, it is contemplated that a single anvil roll (not shown) may extend in the cross-machine direction across all or part of the width of the assemblage 113. For example, the single anvil roll may have a length equal to the width of the assemblage 113 at the side panel strips 118. The anvil roll may have respective bonding and cutting segments toward the opposite ends thereof to correspond to the positions of the side panel strips 118 as the assemblage 113 passes the apparatus. The bonding rolls 216 are still transversely spaced from each other and are in opposed relationship with the single anvil roll at the locations of the bonding and cutting segments of the anvil roll to define the nips 219.

It is also contemplated that a single bonding roll (not shown) may extend transversely in opposed relationship with the single anvil roll along the length of the anvil roll to define a nip that extends along substantially the length of the anvil roll. It is further contemplated that the anvil roll may have cutting and bonding segments thereon for bonding and/or cutting portions of the assemblage 113 intermediate the side panel strips 118, such as those portions of the assemblage which later define the waist end edges 72 of the pants 20.

At least one cutting segment may even extend across the full width of the single anvil roll to cut the assemblage 113 into discrete, partially assembled pants 102. In such an embodiment, the bonding and cutting apparatus 180 may eliminate the need for the cutter 186 shown in FIG. 4 and described later herein.

FIG. 10 illustrates an alternative embodiment of the apparatus 180 in which the anvil roll outer surface 320 comprises a bonding segment 330 having a length shorter than the bonding segment 230 of the anvil roll outer surface 220 of FIG. 7. The shorter bonding segment 330 is intended to mechanically bond the fastening component 170 to the side panel strip 118 corresponding to the back side panel 134 as each pair of training pants 102 passes through the nip 219. The front side panel 34 itself may function as a fastening component so that no mechanical bonding is necessary on the side panel strip 118 corresponding to the front side panel.

FIG. 11 illustrates another alternative embodiment of the apparatus 180 in which the anvil roll outer surface 420 comprises a pair of bonding segments 430a, 430b and a pair of cutting segments 436a, 436b. The cutting segments 436a, 436b are circumferentially spaced from each other and are configured for cutting away portions of the respective side panel strips 118, e.g., to provide the angled and/or curved leg end edges 70 of the front and/or back side panels 34, 134 of the pants 102. The cutting segments 436a, 436b comprise blades 438a, 438b extending transversely and circumferentially of the outer surface 420 of the anvil roll to define first and second cutting patterns which are substantially similar to those defined by the cutting segment 236 of the anvil roll outer surface 220 of FIG. 7.

One of the bonding segments 430a is substantially the same as the bonding segment 230 of the anvil roll outer surface 220 of FIG. 7. The other bonding segment 430b extends circumferentially of the anvil roll outer surface 420 intermediate the blades 438a, 438b of the cutting segments 436a, 436b. In the illustrated embodiment, end portions of the bonding segment 430b circumferentially overlap the cutting segments 436a, 436b, i.e., the projections (not shown but substantially the same as the projections 222 of FIG. 7) of the bonding segment at these end portions are generally transversely adjacent the blades 438a, 438b of the cutting segments. However, it is understood that the ends of the bonding segment 430b may not circumferentially overlap the cutting segments 436a, 436b, as long as the ends of the bonding segment 430a, 430b are positioned generally circumferentially adjacent to the ends of the cutting segments.

Operation of the apparatus of the alternative embodiment of FIG. 11 is similar to that described previously for the embodiment of FIG. 7 with the exception that as the first cutting segment 436a exits the nip 219 upon rotation of the anvil roll, the bonding segment 430*b* intermediate the cutting segments 436*a*, 436*b* is disposed within the nip until the anvil roll rotates further to a position in which the second cutting segment 436*b* defines the nip together with the bonding roll 216. As a result, there is less of a transition (e.g., a lesser change in surface height between the blade 438*a* and the outer ends of the projections 222 of the bonding segment 430*b* of the anvil roll outer surface 420) as the anvil rotates between the first cutting segment 436*a* and the second cutting segment 436*b*. For example, if the bonding segment 430*b* is omitted, there would be a greater height transition (e.g., from the blade height to the reference surface, or reference diameter) following rotation of the first cutting segment 436*a* through the nip. Where the anvil roll 210 and bonding roll 216 remain in contact with each other throughout rotation of the anvil roll, a lesser change in surface height between the cutting segments 436*a*, 436*b*, reduces the impact of the blade 438*b* with the bonding roll as the blade forming the second cutting segment 436*b* enters the nip 219.

While the bonding segments 230, 330, 430 and cutting segments 236, 436*a*, 436*b* of the illustrated embodiments of FIGS. 6–11 are disposed on the anvil roll outer surface 220, 320, 420, it is understood that the bonding segments and cutting segments may instead be disposed on the bonding roll 216. It is also contemplated that one or more bonding segments may be disposed on the anvil roll 210 while one or more cutting segments are disposed on the bonding roll 216, or vice versa, without departing from the scope of this invention.

Also, the apparatus and method illustrated herein is a generally sequential mechanical bonding and cutting operation in which the training pants 102 are first mechanically bonded, then subjected to a cutting operation, and, in certain embodiments, are subjected to further mechanical bonding. However, it is understood that the mechanical bonding and cutting may be conducted in any sequential order and remain within the scope of this invention. It is also contemplated that the apparatus 180 may be configured such that mechanical bonding and cutting of the training pants 102 occur simultaneously. For example a bonding segment and cutting segment may at least partially concurrently define the nip 219 upon rotation of the anvil roll 210, such as where the bonding segment and cutting segment are disposed at substantially the same circumferential location of the anvil roll outer surface.

After passing the mechanical cutting and bonding apparatus 180, the assemblage 113 is passed through the cutter 186 which selectively cuts the assemblage into discrete, partially assembled training pants 102. Such cutters 186 are generally known to those skilled in the art and can include, for example, the combination of a cutting roll 187 and an anvil roll 188 through which the web travels.

The anvil roll 188 can include a hardened steel rotating roll while the cutting roll 187 can include one or more flexible hardened steel blades clamped onto another rotating roll. The pinching force between the blade on the cutting roll 187 and the anvil roll 188 creates the cut. The cutting roll 187 can have one or more blades depending upon the desired distance between the cuts. The cutter 186 can further be configured to provide a spacing between the individual cut pieces after they are cut. Such a spacing can be provided by transferring the cut pieces away from the cutter at a higher speed than the speed at which the web is provided to the cutter.

As various changes could be made in the above constructions and methods, without departing from the scope of the invention, it is intended that all matter contained in the above description and shown in the accompanying drawings shall be interpreted as illustrative and not in a limiting sense.

When introducing elements of the invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed element.

What is claimed is:

1. A method of mechanically bonding and cutting an article, having longitudinally opposite ends, during assembly thereof, said method comprising:
   transporting the article in a machine direction during assembly thereof such that at least part of the article passes through a nip as the article is transported in the machine direction;
   mechanically bonding a portion of the article at said nip as said article passes through the nip; and
   cutting a portion of the article at said nip intermediate its longitudinal ends and separate from said bonded portion as said article passes through the nip.

2. A method as set forth in claim 1 wherein the mechanical bonding step is performed prior to the cutting step.

3. A method as set forth in claim 2 wherein the bonded portion of the article is a first bonded portion thereof, said method further comprising mechanically bonding a portion of the article separate from the first bonded portion and the cut portion of the article to define a second bonded portion thereof, said cutting step being performed prior to mechanically bonding said second bonded portion of the article.

4. A method as set forth in claim 1 wherein the nip is defined in part by a rotatable roll having a circumferential outer surface comprising a bonding segment configured for mechanically bonding the article and a cutting segment configured for cutting the article, the mechanical bonding step comprising rotating the roll such that the nip is in part defined by the bonding segment of the outer surface of the roll, the cutting step comprising rotating the roll such that the nip is in part defined by the cutting segment of the outer surface of the roll.

5. A method as set forth in claim 4 wherein the article has a length in the machine direction, said method further comprising rotating the roll through one complete revolution as the full length of the article passes through the nip.

6. A method as set forth in claim 1 wherein the mechanical bonding comprises ultrasonic bonding.

7. A method as set forth in claim 1 wherein the article has a longitudinal axis, a transverse axis, and first and second longitudinal ends generally defining a length of the article, said transporting step comprising transporting the article in the machine direction such that the article passes, first longitudinal end first, through said nip, the cutting step comprising cutting a portion of the article intermediate the longitudinal ends thereof to remove said cut portion from the article to thereby at least in part define leg openings of the article.

8. A method as set forth in claim 7 wherein the mechanical bonding step is performed prior to the cutting step.

9. A method as set forth in claim 1 wherein the article comprises disposable pants having a side panel extending transverse to the machine direction in which the pants are transported, said transporting step comprising transporting the pants in the machine direction such that the side panel passes through the nip as the pants are transported in the machine direction, the mechanical bonding step comprising mechanically bonding a portion of the side panel as the side panel passes through the nip, the cutting step comprising cutting a portion of the side panel separate from the bonded portion as the side panel passes through the nip.

10. A method as set forth in claim 9 wherein the pants comprises first and second side panels spaced from each other in the machine direction and extending generally transverse to the machine direction in which the pants are transported, the transporting step comprising sequentially passing the side panels through the nip as the pants are transported in the machine direction, the mechanical bonding step comprising mechanically bonding a portion of one of the first and second side panels as the side panels pass through the nip, the cutting step comprising cutting a portion of one of the first and second side panels separate from said bonded portion as the side panels pass through the nip.

11. A method as set forth in claim 10 further comprising mechanically bonding a portion of another one of said first and second side panels.

12. A method as set forth in claim 11 wherein the cutting step is performed after mechanically bonding a portion of one of said first and second side panels and prior to mechanically bonding a portion of another one of said first and second side panels.

13. A method as set forth in claim 10 further comprising cutting a portion of another one of said first and second side panels as the side panels pass through the nip.

14. A method as set forth in claim 1 further comprising positioning a fastening component on the article upstream of the nip, said transporting step comprising passing said article and fastening component together through the nip as the article is transported in the machine direction, the bonding step comprising mechanically bonding the fastening component to the article as said article and fastening component pass through the nip.

15. A method as set forth in claim 1 wherein the cutting step comprises cutting said portion of the article in a direction at least in part transverse to the machine direction in which the article is transported.

16. A method as set forth in claim 1 wherein the mechanically bonding step comprises mechanically bonding a portion of the article at said nip intermediate its longitudinal ends as the article passes through the nip.

* * * * *